US00PP28209P3

(12) United States Plant Patent
Uchneat

(10) Patent No.: US PP28,209 P3
(45) Date of Patent: Jul. 18, 2017

(54) ***DAHLIA* PLANT NAMED 'G13532'**

(50) Latin Name: *Dahlia variabilis*
Varietal Denomination: G13532

(71) Applicant: Michael S. Uchneat, Bellefonte, PA (US)

(72) Inventor: Michael S. Uchneat, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 12 days.

(21) Appl. No.: 14/756,441

(22) Filed: Sep. 4, 2015

(65) Prior Publication Data

US 2017/0071104 P1 Mar. 9, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

(56) References Cited

PUBLICATIONS

National Gardening Association 2016 Plants Database *Dahlia* (*Dahlia* Dahlightful Lively Lavender) retrieved on Nov. 2, 2016, retrieved from the Internet at <http://garden.org/plants/view/710313/Dahlia-Dahlia-Dahlightful-Lively-Lavender/> pp. 1-3.*
Proven Winners Image 2016 Dahlightful Lively Lavender Beauty retrieved on Nov. 2, 2016, retrieved from the Internet at <https://www.provenwinners.com/images/dahlightful-lively-lavender-beauty-monojpg> pp. 1-2.*

* cited by examiner

*Primary Examiner* — June Hwu
(74) *Attorney, Agent, or Firm* — C. A. Whealy

(57) ABSTRACT

A new and distinct cultivar of *Dahlia* plant named 'G13532', characterized by its compact and upright plant habit; vigorous growth habit; freely branching habit; very dark brown-colored leaves; early and freely flowering habit; and semi-double type inflorescences with purple violet-colored ray florets.

1 Drawing Sheet

Botanical designation: *Dahlia variabilis.*
Cultivar denomination: 'G13532'.

BACKGROUND OF THE INVENTION

The present invention relates to a new and distinct cultivar of *Dahlia* plant, botanically known as *Dahlia variabilis* and hereinafter referred to by the name 'G13532'.

The new *Dahlia* plant is a product of a planned breeding program conducted by the Inventor in Bellefonte, Pa. The objective of the breeding program is to create new vigorous *Dahlia* plants that have dark-colored leaves, large attractive inflorescences and reduced sensitivity to Powdery Mildew.

The new *Dahlia* plant originated from a cross-pollination in Bellefonte, Pa. in November, 2012 of a proprietary selection of *Dahlia variabilis* identified as code number 3173-3, not patented, as the female, or seed, parent with a proprietary selection of *Dahlia variabilis* identified as code number 3182-3, not patented, as the male, or pollen, parent. The new *Dahlia* plant was discovered and selected by the Inventor as a single flowering plant from within the progeny of the stated cross-pollination in a controlled greenhouse environment in Bellefonte, Pa. in June, 2013.

Asexual reproduction of the new *Dahlia* plant by vegetative terminal cuttings in a controlled greenhouse environment in Bellefonte, Pa. since July, 2013 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'G13532'. These characteristics in combination distinguish 'G13532' as a new and distinct *Dahlia* plant:

1. Compact and upright plant habit.
2. Vigorous growth habit.
3. Freely branching habit.
4. Very dark brown-colored leaves.
5. Early and freely flowering habit.
6. Semi-double type inflorescences with purple violet-colored ray florets.

Compared to plants of the female parent selection, plants of the new *Dahlia* differ primarily in the following characteristics:

1. Plants of the new *Dahlia* are more vigorous than plants of the female parent selection.
2. Plants of the new *Dahlia* have semi-double type inflorescences whereas plants of the female parent selection have single type inflorescences.
3. Plants of the new *Dahlia* and the female parent selection differ in ray floret color as plants of the female parent selection have lavender purple-colored ray florets.

Compared to plants of the male parent selection, plants of the new *Dahlia* differ primarily in the following characteristics:

1. Plants of the new *Dahlia* are more vigorous than plants of the male parent selection.
2. Leaves of plants of the new *Dahlia* are darker in color than leaves of plants of the male parent selection.
3. Plants of the new *Dahlia* flower earlier than plants of the male parent selection.
4. Plants of the new *Dahlia* and the male parent selection differ in ray floret color as plants of the male parent selection have salmon orange-colored ray florets.

Plants of the new *Dahlia* can be compared to plants of *Dahlia* 'Zone Ten', disclosed in U.S. Plant Pat. No. 19,885. In side-by-side comparisons conducted in Bellefonte, Pa., plants of the new *Dahlia* differed primarily from plants of 'Zone Ten' in the following characteristics:

1. Plants of the new *Dahlia* had semi-double type inflorescences whereas plants of 'Zone Ten' had single type inflorescences.
2. Plants of the new *Dahlia* and 'Zone Ten' differed in ray floret color as plants of 'Zone Ten' had soft pink and white bi-colored ray florets.

Plants of the new *Dahlia* can be compared to plants of *Dahlia* 'HDPU165', disclosed in U.S. Plant Pat. No. 23,299. In side-by-side comparisons conducted in Bellefonte, Pa., plants of the new *Dahlia* differed primarily from plants of 'HDPU165' in the following characteristics:

1. Plants of the new *Dahlia* were more vigorous than plants of 'HDPU165'.
2. Plants of the new *Dahlia* had semi-double type inflorescences whereas plants of 'HDPU165' had single type inflorescences.
3. Plants of the new *Dahlia* and 'HDPU165' differed in ray floret color as plants of 'HDPU165' had red purple-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the right side of the sheet is a side perspective view of a typical flowering plant of 'G13532' grown in a container.

The photograph on the left side of the sheet is a close-up view of a typical inflorescence of 'G13532'.

DETAILED BOTANICAL DESCRIPTION

The aforementioned photographs and the following observations and measurements describe plants grown during the summer in 10-cm containers in an outdoor nursery in Bonsall, Calif. and under cultural practices typical of commercial potted *Dahlia* production. During the production of the plants, day temperatures averaged 27° C., night temperatures averaged 18° C. and light levels ranged from 7,000 to 10,000 foot-candles. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Dahlia variabilis* 'G13532'.

Parentage:

*Female, or seed, parent.*—Proprietary selection of *Dahlia variabilis* identified as code number 3173-3, not patented.

*Male, or pollen, parent.*—Proprietary selection of *Dahlia variabilis* identified as code number 3182-3, not patented.

Propagation:

*Type.*—By vegetative terminal cuttings.

*Time to initiate roots, summer.*—About 7 to 10 days at ambient temperatures about 22° C. to 27° C.

*Time to initiate roots, winter.*—About 10 to 14 days at ambient temperatures about 18° C. to 23° C.

*Time to produce a rooted plant, summer.*—About three to four weeks at ambient temperatures about 22° C. to 27° C.

*Time to produce a rooted plant, winter.*—About four weeks at temperatures about 18° C. to 23° C.

*Root description.*—Medium in thickness, fleshy and fibrous; close to white to creamy white in color, actual color of the roots is dependent on substrate composition, water quality, fertilizers, substrate temperature and age of roots; tuber development has not been observed on plants of the new *Dahlia*.

*Rooting habit.*—Freely branching; medium density.

Plant description:

*Plant and growth habit.*—Compact and upright plant form; inverted triangle; freely branching habit with about four lateral branches developing per plant, each lateral with potentially one to two secondary laterals developing per node; pinching enhances lateral branch development; inflorescences held above the foliar plane on strong peduncles; vigorous growth habit.

*Plant height.*—About 27.5 cm.

*Plant diameter or spread.*—About 20.5 cm.

*Lateral branches.*—Length: About 25.5 cm. Diameter: About 6 mm. Internode length: About 4.5 cm to 5 cm. Strength: Strong. Aspect: Erect. Texture: Smooth, glabrous. Luster: Matte. Color: Close to 187A.

Leaf description:

*Arrangement.*—Opposite; simple.

*Length.*—About 7.3 cm.

*Width.*—About 8.8 cm.

*Shape.*—Deeply five-lobed with parallel to divergent sinuses.

*Apex.*—Acute.

*Base.*—Attenuate.

*Margin.*—Serrulate.

*Venation pattern.*—Pinnate.

*Texture, upper and lower surfaces.*—Smooth, glabrous; leathery and slightly coarse.

*Luster, upper and lower surfaces.*—Matte.

*Color.*—Developing leaves, upper surface: Close to N137A. Developing leaves, lower surface: Close to 197A. Fully expanded leaves, upper surface: Slightly more green than 200A, close to black in appearance; venation, close to 200A. Fully expanded leaves, lower surface: Close to 148A; venation, close to 200B to 200C.

*Petioles*.—Length: About 4.4 cm. Diameter: About 4 mm. Strength: Strong. Texture, upper and lower surfaces: Smooth, glabrous. Luster, upper and lower surfaces: Glossy. Color, upper surface: Close to N200A. Color, lower surface: Close to 200B.

Inflorescence description:

*Appearance and arrangement*.—Semi-double inflorescence form with ray florets forming acropetally on a receptacle; inflorescences positioned above the foliar plane on strong peduncles; inflorescences face mostly upright to outwardly; freely flowering habit with about ten inflorescence buds and open inflorescences at one time.

*Fragrance*.—Faint; slightly sour.

*Time to flower*.—Early flowering habit, plants begin flowering about five weeks after planting; plants flower continuously from late spring through the autumn in Southern California.

*Post-production longevity*.—Inflorescences maintain good substance for about five days on the plant; inflorescences persistent.

*Inflorescence buds*.—Height: About 2 cm. Diameter: About 1.2 cm. Shape: Ovoid to conical. Color: Close to N81A to N81B.

*Inflorescence size*.—Diameter: About 6.7 cm. Depth (height): About 2.8 cm. Disc diameter: About 2 cm.

*Receptacles*.—Height: About 1 cm. Diameter: About 3.6 cm. Shape: Shallow bowl-shape. Color: Close to 200A and 200B to 200C.

*Ray florets*.—Quantity per inflorescence: About 32 arranged in three whorls. Length: About 3.4 cm. Width: About 1.7 cm. Shape: Obovate. Apex: Shallowly emarginate. Base: Attenuate. Margin: Entire. Aspect: Initially upright to roughly perpendicular to the peduncle; somewhat concave. Texture, upper and lower surfaces: Longitudinally ridged, glabrous. Luster, upper and lower surfaces: Matte, velvety. Color: When opening, upper surface: Close to N78A. When opening, lower surface: Close to N78B to N78C. Fully opened, upper surface: Close to N81C; color becoming closer to N78C to N78D with development. Fully opened, lower surface: Close to N81D; color becoming closer to N78D with development.

*Disc florets*.—Quantity per inflorescence: About 62. Length: About 1.5 cm. Diameter: About 3 mm. Shape: Tubular, elongated; apices acute. Texture: Smooth, glabrous. Luster: Satiny. Color, when opening: Apex: Close to 175B. Mid-section: Close to 167B. Base: Close to 165C. Color, fully opened: Apex: Close to 175B. Mid-section: Close to N167B. Base: Close to 162B.

*Phyllaries*.—Quantity per inflorescence: About 40 arranged in about four to five whorls; inner whorls are membraneous, thin and translucent. Length: About 1.6 cm. Width: About 6 mm. Shape: Elliptical. Apex: Acute. Base: Truncate. Margin: Entire. Texture, upper and lower surfaces: Smooth, glabrous. Luster, upper and lower surfaces: Shiny. Color, upper and lower surfaces: Close to 195A.

*Peduncles*.—Length, terminal peduncle: About 9.5 cm. Diameter: About 2 mm. Aspect: Mostly erect. Strength: Strong. Texture: Smooth, glabrous. Luster: Matte. Color: Close to 200A.

*Reproductive organs*.—Present on disc florets only; ray florets without visible reproductive organs. Androecium: Quantity per floret: Five. Filament length: About 4 mm. Filament color: Close to 145D. Anther shape: Lanceolate. Anther length: About 4 mm. Anther color: Close to N163D. Pollen amount: Moderate. Pollen color: Close to 23A. Gynoecium: Quantity per floret: One. Pistil length: About 1.8 cm. Style length: About 1.2 cm. Style color: Close to NN155D. Stigma shape: Bi-parted. Stigma color: Close to 21B. Ovary color: Close to 155A. Seeds and fruits: Seed and fruit development have not been observed on plants of the new *Dahlia*.

Disease & pest resistance: Plants of the new *Dahlia* have not been observed to be resistant to pathogens and pests common to *Dahlia* plants.

It is claimed:

1. A new and distinct *Dahlia* plant named 'G13532' as illustrated and described.

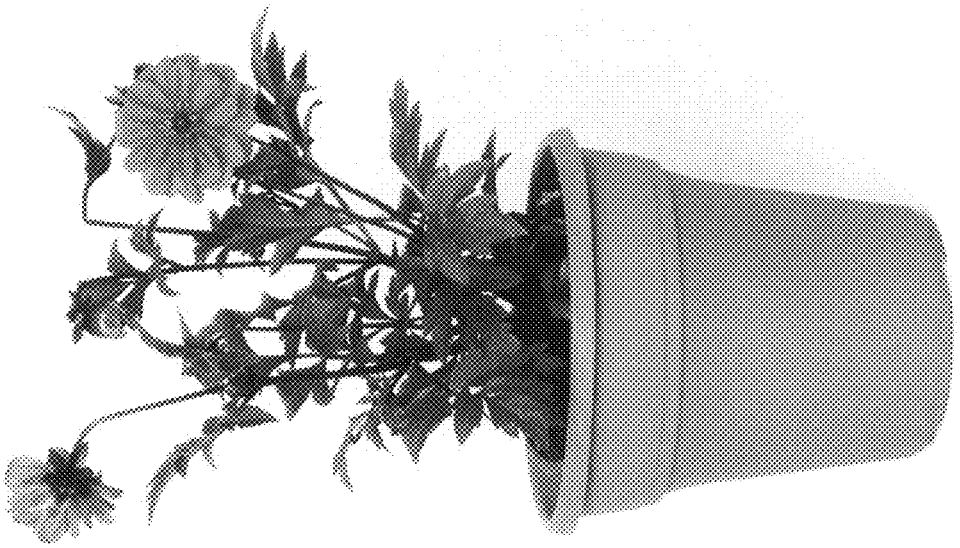
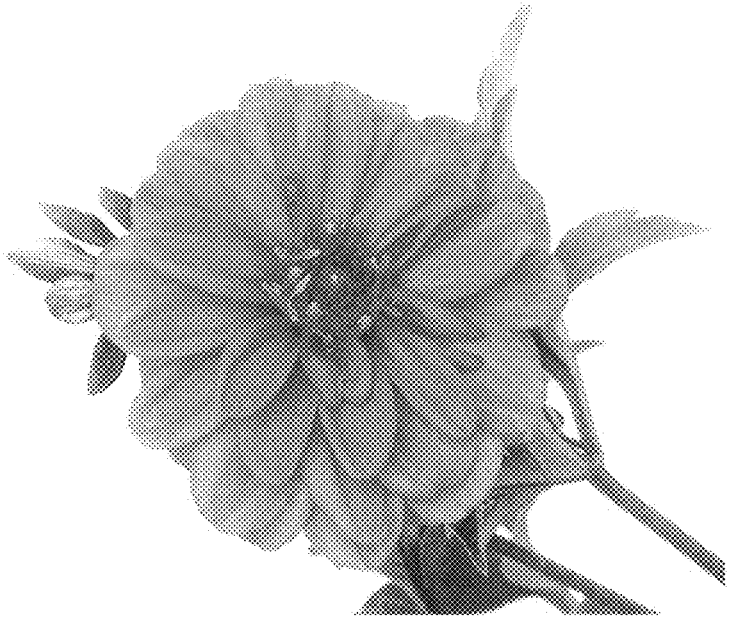

* * * * *